(12) United States Patent
Gruskin et al.

(10) Patent No.: US 6,756,518 B2
(45) Date of Patent: Jun. 29, 2004

(54) SCAR REDUCTION

(75) Inventors: Elliott A. Gruskin, Killingworth, CT (US); Christofer T. Chistoforou, Pleasanton, CA (US)

(73) Assignee: United States Surgical Corporation, Norwalk, CT (US)

( * ) Notice: Subject to any disclaimer, the term of this patent is extended or adjusted under 35 U.S.C. 154(b) by 181 days.

(21) Appl. No.: 10/058,182

(22) Filed: Jan. 25, 2002

(65) Prior Publication Data

US 2003/0023209 A1 Jan. 30, 2003

Related U.S. Application Data

(63) Continuation of application No. 09/519,006, filed on Mar. 3, 2000, now Pat. No. 6,410,519.
(60) Provisional application No. 60/122,814, filed on Mar. 4, 1999.

(51) Int. Cl.[7] .................... A61F 13/00; A01N 43/04; A61M 35/00
(52) U.S. Cl. .................... 602/48; 602/43; 602/49; 514/59; 604/290; 604/304
(58) Field of Search ............. 602/41–59; 424/443–444; 604/304–308

(56) References Cited

U.S. PATENT DOCUMENTS

| | | | |
|---|---|---|---|
| 2,988,455 A | 6/1961 | Rosenberg et al. | 106/169 |
| 3,042,667 A | 7/1962 | Flodin et al. | 260/209 |
| 4,308,254 A | 12/1981 | Tayot et al. | 424/124 |
| 4,339,230 A | 7/1982 | Hill | 416/226 |
| 4,339,360 A | 7/1982 | Shimizu et al. | 524/28 |
| 4,370,476 A | 1/1983 | Usher et al. | 536/113 |
| 4,591,638 A | 5/1986 | Ahrgren et al. | 536/51 |
| 4,963,666 A | 10/1990 | Malson | 536/55.1 |
| 4,988,358 A | 1/1991 | Eppley et al. | 623/16 |
| 5,092,883 A | 3/1992 | Eppley et al. | 623/11 |
| 5,336,501 A | 8/1994 | Czech et al. | 424/445 |
| 5,496,371 A | 3/1996 | Eppley et al. | 623/16 |
| 5,502,042 A | 3/1996 | Gruskin et al. | 514/59 |
| 5,662,904 A * | 9/1997 | Ferguson et al. | 424/130.1 |

FOREIGN PATENT DOCUMENTS

| | | |
|---|---|---|
| EP | 562862 A1 | 9/1993 |
| EP | 562864 A1 | 9/1993 |
| WO | 9200570 | 1/1992 |
| WO | 9309176 | 5/1993 |

* cited by examiner

Primary Examiner—Kim M. Lewis

(57) ABSTRACT

A method of reducing scar formation at a wound site includes contacting the wound site with an effective scar reducing amount of a cross-linked polysaccharide having a positive charge and thereby reducing scar formation as the wound site heals. Such polysaccharide include bioabsorbable cross-linked dextrans or alginates. The positive charge may be provided by diethylaminoethyl (DEAE) moieties. The cross-linked polysaccharide can be applied to the wound site as a powder or bead. The cross-linked polysaccharide may also be contained in a composition including a pharmaceutically acceptable vehicle. Biocompatable surgical devices are provided with an effective scar reducing amount of a cross-linked polysaccharide having a positive charge which reduce scar formation at healing wound sites. A method of reducing TGF-β activity is also provided.

17 Claims, 7 Drawing Sheets

Histology at day 28 for bead treated and control wounds

Control

Treated

Histology at day 7 for bead treated and control wounds
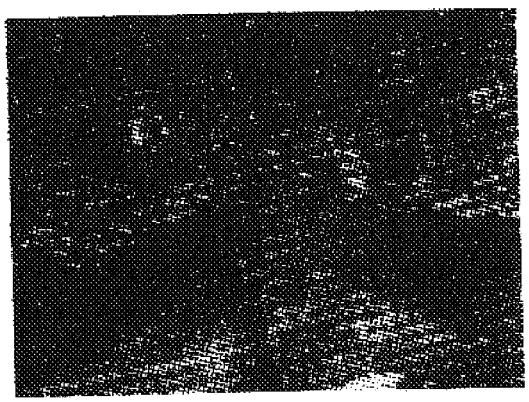 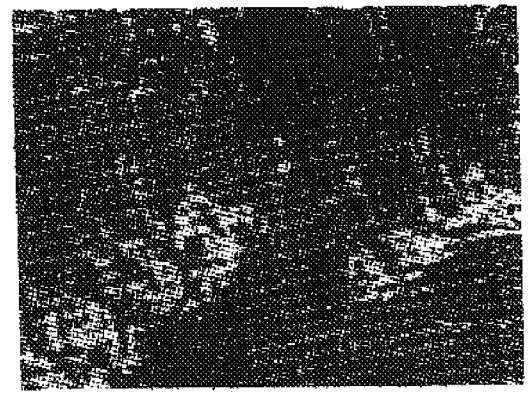
Treated  
*Fig. 4*
Control  
*Fig. 5*

Histology at day 10 for bead treated and control wounds

Control

Treated

Histology at day 14 for bead treated and control wounds

Control

Treated

Histology at day 21 for bead treated and control wounds

Control

Treated

SCAR REDUCTION

This application is a continuation of U.S. patent application Ser. No. 09/519,006 filed Mar. 3, 2000 now U.S. Pat. No. 6,410,519, which claims benefit of Provisional Application No. 60/122,814, filed Mar. 4, 1999.

BACKGROUND

1. Technical Field

This disclosure relates to reduction of scars associated with healing tissue. More particularly, wounds are treated with an oxidized cross-linked polysaccharide having a chemically induced charge.

2. Background of Related Art

Dextran is a polysaccharide which is produced from sucrose by bacteria belonging to the genera Leuconostoc, Streptococcus and Lactobacillus, all of which belong to the family Lactobacillaceae. The majority of known dextrans are formed by strains of Leuconostoc mesenteroides. A detailed discussion of dextran is provided in the Encyclopedia of Polymer Science and Engineering, Vol. 4, pp. 752 et seq. (1986) (John Wiley & Sons), hereby incorporated by reference. Dextran, in which 1→6 linkages predominate, may be represented as follows:

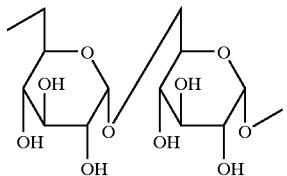

Certain dextran derivatives are well known. Dextran which is crosslinked with epichlorohydrin is described in U.S. Pat. No. 3,042,667 and in British Patent No. 1,013,585 and is commercially available under the tradename SEPHADEX from Pharmacia Corp., Piscataway, N.J. Epichlorohydrin ($CH_2OCHCH_2Cl$) reacts with the pendant hydroxyl groups on dextran to form ether bound bridges between dextran chains.

Various other derivatives of dextran are known. For example, see U.S. Pat. No. 4,963,666, (ester crosslinking), U.S. Pat. No. 4,591,638 (ester crosslinking), U.S. Pat. No. 2,988,455 (oxidized), U.S. Pat. No. 4,370,476 (ferric hydroxide complexes), U.S. Pat. No. 4,339,360 (activated oxidized) and U.S. Pat. No. 4,308,254 (oxidized support).

Dextran has been employed in the treatment of wounds. For example, an insoluble hydrophilic cross-linked dextran polymer in powder form has been used for the debridement of wounds, i.e., the removal of foreign bodies, pus, exudates and irrevocably damaged and devitalized tissue from tissue wounds. This dextran polymer, which is formed by crosslinking dextran with epichlorohydrin, is applied to heavily exudating wounds, allowed to gel and then washed out. The crosslinked dextran, commercially known as DEBRISAN®, absorbs the exudates, including the components that tend to impede tissue repair. Consequently, this composition promotes wound healing by retarding eschar formation and by keeping lesions soft and pliable.

Dextran derivatives have been used to promote hard tissue growth and repair and soft connective tissue growth and repair in mammals as described in U.S. Pat. Nos. 4,988,358 and 5,092,883, respectively. In one aspect, SEPHADEX, a cross-linked dextran available from Pharmacia Corp., (Piscataway, N.J.), linked with diethylaminoethyl (DEAE) functional groups as a basic anion exchanger is used for promoting soft tissue growth and repair by applying an effective quantity thereof to a site of tissue defect. The chemically induced surface charges promote soft connective tissue formation. In U.S. Pat. No. 5,092,883, examples 4 and 5 indicate that positively charged DEAE-Sephadex beads are associated with stimulation effect on fibroblastic activity and that defects treated with the beads were filled with dense, highly cellular soft connective tissue. Wounds with positively charged beads are shown to be stronger than control wounds. There is, however, no recognition that scarring, which may typically be associated with healing wounds, can be reduced.

A scar is the mark left in the skin or an internal organ by new connective tissue that replaces tissue which has been injured by, e.g., burn, ulcer, abrasion, incision, etc. Scars may be viewed as unsightly defects which can result in psychological discomfort of people bearing such scars. As a result, the search for effective scar reducing measures has been ongoing. For example, as described in International Application No. PCT/GB92/00570, a composition for use in the treatment of wounds to inhibit scar tissue formation includes an activity-inhibiting amount of a growth factor neutralizing agent. It is therein indicated that TGF-β appears to be highly active in connection with organization of collagen leading to the formation of scar tissue. In accordance with PCT/GB92/00570, scar tissue formation is reduced by neutralizing TGF-β.

SUMMARY

A method of reducing scar formation at a wound site includes contacting the wound site with an effective scar reducing amount of a cross-linked polysaccharide having a positive charge and thereby reducing scar formation as the wound site heals. Such polysaccharide include bioabsorbable cross-linked dextrans or alginates. The positive charge may be provided by diethylaminoethyl (DEAE) moieties. The cross-linked polysaccharide can be applied to the wound site as a powder or bead. The cross-linked polysaccharide may also be contained in a composition including a pharmaceutically acceptable vehicle. Biocompatable surgical devices provided with an effective scar reducing amount of a cross-linked polysaccharide having a positive charge reduce scar formation at healing wound sites.

A method of reducing the activity of the TGF-β includes applying an effective TGF-β activity reducing amount of a cross-linked polysaccharide having a positive change to a locus having TFG-β activity.

BRIEF DESCRIPTION OF THE DRAWINGS

FIG. 4 is a depiction of a control wound site at 7 days post-wounding;

FIG. 5 is a depiction of a wound site treated with degradable DEAE dextran at 7 days post-wounding;.

DETAILED DESCRIPTION OF THE PREFERRED EMBODIMENTS

Figure 1:
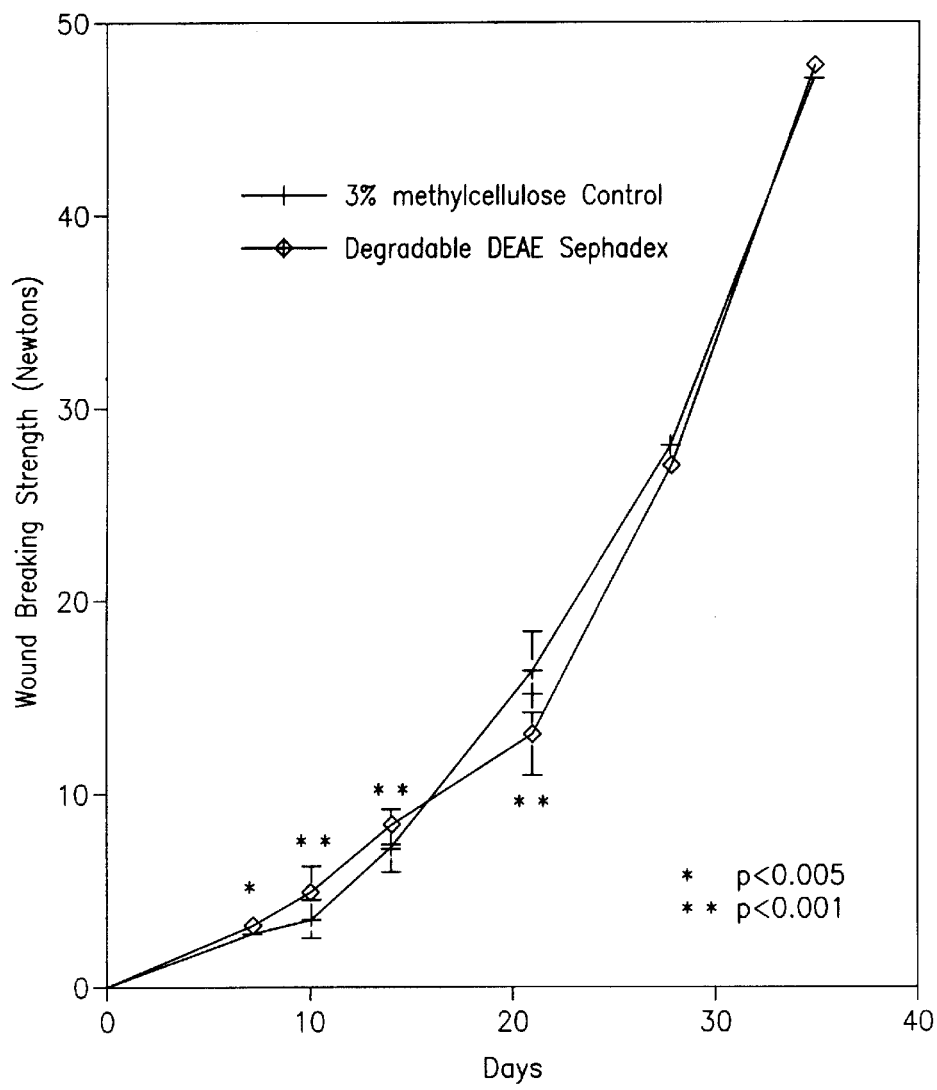
FIG. 1 is a graphic depiction of wound breaking strength in terms of Newtons over time comparing effect of degradable DEAE dextran with a methycellulose control.

The present method of reducing scar formation at a wound site includes contacting the wound site with an effective scar reducing amount of a cross-linked polysaccharide having a positive charge. The polysaccharide can be ionically or covalently cross-linked. Among the ionically cross-linked polysaccharides useful in preparing the present wound treatment compositions are alginic acid and pectic acid which complex with certain multivalent ions such as $Ca^{++}$ to provide ionic cross-linking. Among the covalently cross-linked polysaccharides, dextran and modified alginates are preferred for use in the present method. Cross-linked dextran is available under the tradename SEPHA-DEX from Pharmacia Corp., (Piscataway, N.J.). Modified, covalently cross-linked alginates can be prepared, for example, as described in PCT WO 93/09176 which is incorporated herein by reference.

In a preferred embodiment, the cross-linked polysaccharide is biodegradable. Any known cross-linked biodedgradable polysaccharide which can be made to carry a positive charge is suitable herein. For example, biodegradable cross-linked dextrans such as those described in U.S. Pat. Nos. 4,963,666 and 4,591,638 are suitable. A biodegradable oxidized cross-linked polysaccharide having a chemically induced positive charge such as that described in U.S. Pat. No. 5,502,042, the contents of which are incorporated herein by reference, is especially preferred.

Positive charges may be associated with cross-linked polysaccharides by any method known in the art. See, for example, U.S. Pat. Nos. 4,988,358 and 5,092,883 to Eppley et al., the disclosures of which are incorporated herein by reference. In the case of oxidized cross-linked polysaccharide, positive chemical charge should be chemically induced on the polysaccharide, preferably prior to oxidation. For example, a positive charge can be provided on the polysaccharide by reaction with diethylamino ethyl chloride. Cross-linked dextran having DEAE groups thereon is commercially available under the name DEAE-SEPHADEX from Pharmacia Corp., Piscataway, N.J. The charged, cross-linked polysaccharide is oxidized to cleave a portion of the monosaccharide units to provide groups terminating in carboxyl groups.

Specifically, for example, in a dextran, the group:

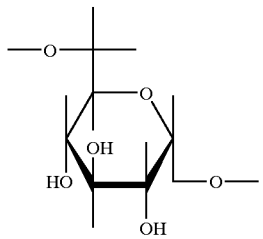

oxidizes to either of the following two structures, depending on the oxidizing agent employed and the oxidizing conditions:

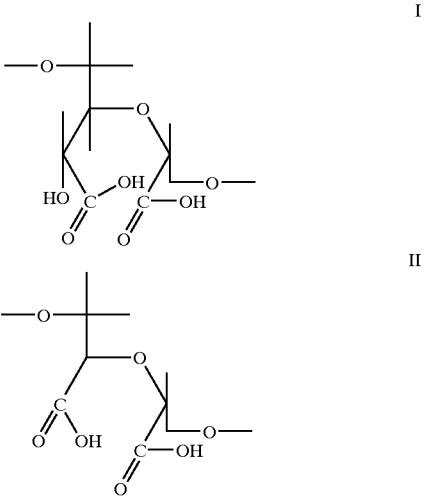

The linkages of structures I and II above are unstable and render the cross-linked polysaccharide biodegradable. The rate of biodegradation can be controlled by controlling the oxidation conditions to regulate the amount of monosaccharide units within the polysaccharides that are converted to structures I and/or II. Preferably, the oxidized, crosslinked polysaccharide will not completely lose its integrity until at least two days after application to a wound site.

Once prepared, the cross-linked positively charged polysaccharide can be applied directly to a wound site. When the wound is caused by traumatic and/or abrasive injury, the wound site is ordinarily debrided to remove extraneous material and reduce chance of infection. The positively charged polysaccharide is then applied to the wound site. In the case of surface wounds, the wound site containing the charged polysaccharide is then covered by bandage or other wound occluding devices known in the art. If the wound runs deep into tissue, after application of the positively charged polysaccharide the wound may be closed by conventional surgical techniques such as suturing, stapling, etc. After sealing the wound site, the wound is allowed to heal while exhibiting markedly reduced scarring. Thus, for example, where DEAE-Sephadex has been oxidized, the beads can be sprinkled directly onto a wound site by sprinkling from a shaker or other container having one or more openings in its lid.

Application of positively charged polysaccharide to a wound in accordance with the present disclosure reduces the activity of TGF-β. Without wishing to be bound by any particular theory, it appears as though scar reduction is effected, at least in part, by the reduction of TGF-β activity.

See International App. No. PCT/GB92/00570. Thus, by application of an effective amount of positively charged polysaccharide to a locus having TGF-β activity, the activity of TGF-β is reduced.

In particularly useful embodiments the cross-linked positively charged polysaccharide such as the oxidized cross-linked charged polysaccharide is mixed with a delivery vehicle to form a paste or fluid which can be applied to a wound. Any pharmaceutically acceptable biocompatible fluid can be used as the delivery vehicle. Where the delivery vehicle is based on water, saline or some other polar fluid, and the charged polysaccharide is biodegradable it may be necessary to take steps to avoid premature hydrolysis. For example, a scar reducing wound treatment can be provided as two separate components, namely the dry components (including the polysaccharide) in one container and the fluid component of the delivery vehicle in another container. The contents of the two containers are mixed shortly (preferably less than one hour) before application to the wound site. As another example, after mixing the polysaccharide and a polar delivery vehicle, the composition can be frozen to avoid premature hydrolysis. The scar reducing wound treatment could be thawed shortly before application to a wound site.

Alternatively, the polysaccharide can be mixed with a delivery vehicle based on a non-polar fluid. Suitable non-polar fluids include, mineral oil, non-ionic surfactants liquid low molecular weight poly(ethylene oxide) and liquid low molecular weight poly(propylene oxide).

The viscosity of the scar reducing cross-linked polysaccharide will determine the method of its application. Thus, for example, low viscosity compositions can be sprayed or poured onto a wound site. Compositions having a paste-like or gel-like viscosity can be applied to a wound site via spatula, syringe or from a tube.

It may be desirable to package the scar reducing cross-linked polysaccharide in a manner which prevents contact of the material with water. Known water impervious packages can be used. Additionally, the atmosphere within the package can be replaced with a dry, inert gas. Alternatively, a desiccant can be placed within the package.

The scar reducing cross-linked polysaccharide can be sterilized using any technique which does not expose biodegradable material to excessive conditions which may cause premature degradation. Accordingly, ethylene oxide or gamma radiation are preferred sterilization methods.

The wound treatment composition including the positively charged polysaccharide may optionally include additives such as fillers, colorants or viscosity modifiers. The wound treatment composition may also include a film-forming component if desired. Additionally, wound treatment composition may include one or more medico-surgically useful substances or therapeutic agent, e.g., those which accelerate or beneficially modify the healing process when particles are applied to a surgical repair site. The therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamicin sulfate, erythromycin or VX glycopeptides) which are slowly released into the tissue can be applied in this manner to aid in combating clinical and sub-clinical infections in a tissue repair site. To promote repair and/or tissue growth, one or several growth promoting factors can be incorporated, e.g., fibroblast growth factor bone morphogenetic protein, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system. It is also contemplated that the medico-surgically useful substance may enhance blood coagulation. Thrombin is one such substance.

The scar reducing positively charged cross-linked polysaccharide may be applied to or incorporated in surgical devices for implantation into patients. For example, sutures can be coated or impregnated with scar reducing polysaccharides and then used to suture a wound. In the case of absorbable sutures, the presence of scar reducing polysaccharide minimizes scar formation at the wound site as the suture is absorbed. Bandages and other occlusive devices can be precoated with scar reducing polysaccharides for convenient application to surface wounds. Prosthetic devices known in the art such as artificial hips may be coated or impregnated with scar reducing polysaccharides. Cosmetic implants such as maxillofacial implants (see, for example, U.S. Pat. Nos. 5,554,194 or 5,496,371) can be provided with a coating of or be impregnated with scar reducing polysaccharides to reduce scarring of surrounding tissue after implantation.

The following non-limiting examples illustrative of the present disclosure.

EXAMPLE

Degradable DEAE Sephadex beads were suspended in a polyethylene glycol gel at a concentration of 10 mg of beads per ml of PEG. The resulting composition was gamma sterilized and packaged in an aluminum tube. The composition was stored at room conditions until time of surgery.

275–350 g male Sprague-Dawley rats were anesthetized and two parallel 6 cm incisions were made, 1.5 cm either side of the spine. Wounds were closed with surgical staples (Multifire premium 35W, United States Surgical Corporation). Approximately 1 ml of composition was applied in one incision and saline was applied in the contralateral wound. At days 7, 10, 14, 21 and 28, the dorsal skin from ten rats were removed and 8 mm strips perpendicular to the incision were excised. A total of three strips were taken from each wound. Matched-pair samples of experimental and control wounds from each rat were placed immediately after harvest into 10% buffered Formalin and embedded in paraffin by routine methods. The wounds were sectioned perpendicular to the incision and stained with hematoxylin and eosin.

There were 15 and 11 nodules in DEAE Sephadex treated samples at day 7 and day 10, respectively. The nodules were small localized bumps where excess material had accumulated. Such accumulation appeared to be the result of stapling on a loose skinned animal. These nodules subsided by day 14. At day 14, the treatment group was similar to the control group with no presence of nodules and this observation continued through day 28.

In wounds with degradable DEAE Sephadex beads at day 7, the beads were found at the base of the wound. The beads were intact spheres staining deep red in color. Histologically there was a mild inflammatory response at day 7 composed primarily of macrophage.

At days 10 and 14 the inflammation began to subside and the beads showed signs of mass loss, evidenced by the lack of deep red staining within the bead.

By days 21 and 28 the inflammation had subsided and the wounds were very well healed. The beads were further degraded as shown by the lighter straining and the presence of few beads. FIGS. 2–11 show representative examples of the histological findings.

Figure 2:
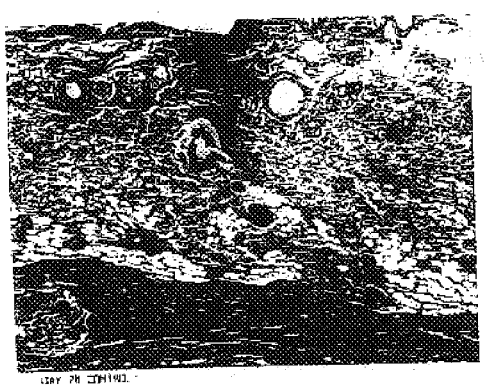
FIG. 2 is a depiction of a control wound site at 28 days post-wounding.
Figure 3:
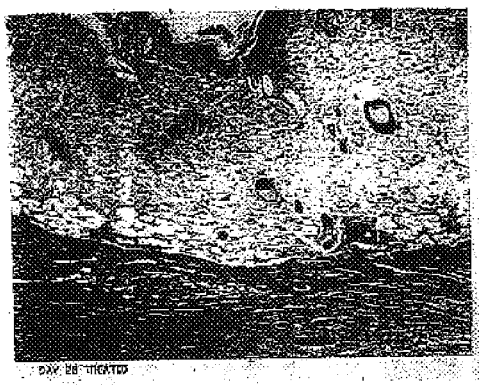
FIG. 3 is a depiction of a wound site treated with degradable DEAE dextran at 28 days post-wounding.
Figure 6:
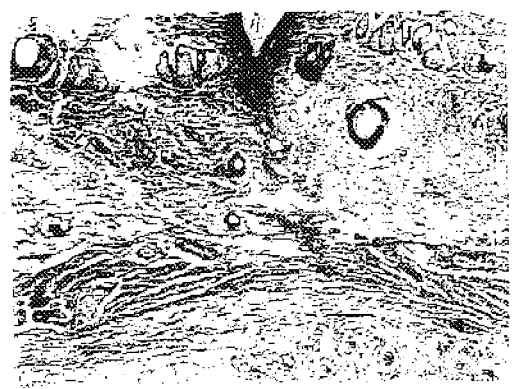
FIG. 6 is a depiction of a control wound site at 10 days post-wounding.
Figure 7:
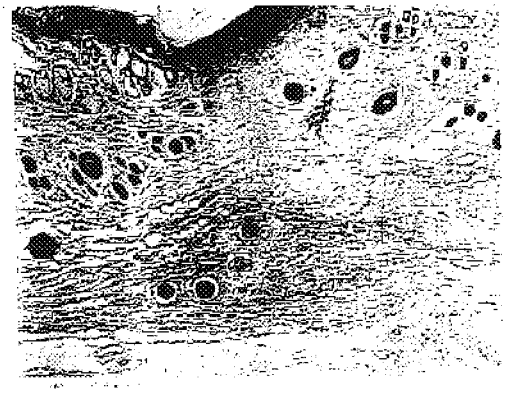
FIG. 7 is a depiction of a wound site treated with degradable DEAE dextran at 10 days post-wounding.
Figure 8:
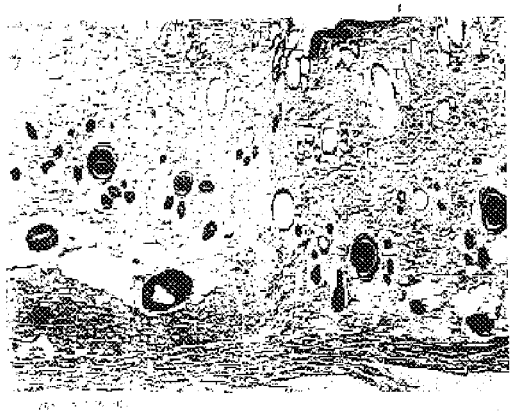
FIG. 8 is a depiction of a control wound site at 14 days post-wounding.
Figure 9:
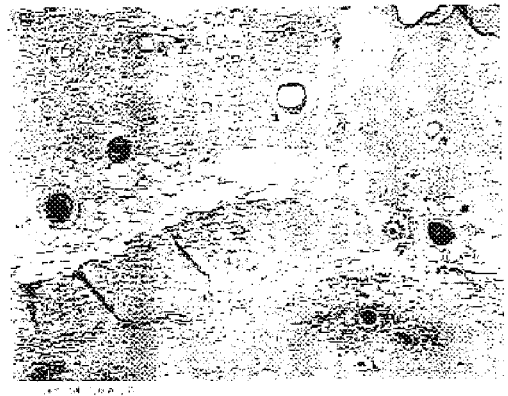
FIG. 9 is a depiction of a wound site treated with degradable DEAE dextran at 14 days post-wounding.
Figure 10:
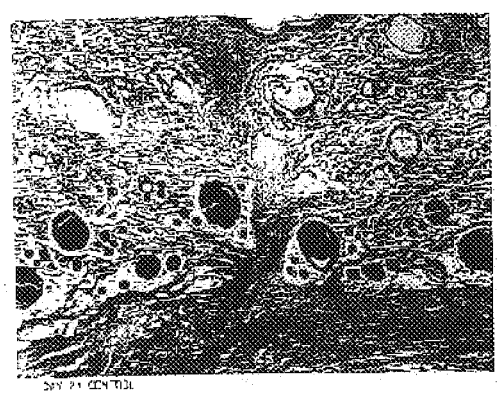
FIG. 10 is a depiction of a control wound site at 21 days post-wounding.
Figure 11:
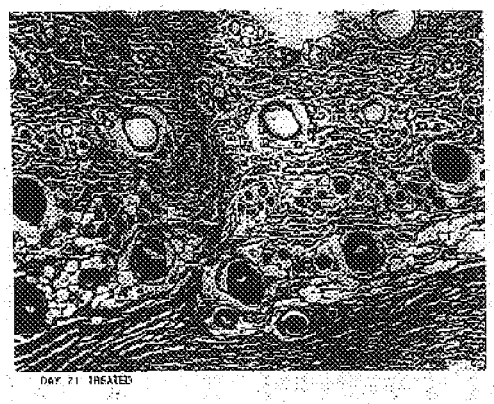
FIG. 11 is a depiction of a wound site treated with degradable DEAE dextran at 21 days post-wounding.

As can be seen from FIGS. 2 and 3, clear reduction in scarring resulted from treatment in accordance with the present disclosure. FIG. 2 shows the control and FIG. 3 the treated incisions 28 days post wounding. The control side shows a normal scar along the incision line. In the treated wound the incision line is not detectable.

In addition, the maximum load tolerated by wound strips prior to breaking was measured with a Tensometer (Monsanto, St. Louis, Mo.). Measurements were not performed on wounds showing evidence of infection, excessive hemorrhage, or poor coaptation. Samples for histology were taken from the cephalic and caudate ends of each wound.

The breaking strength for each wound was paired with its contralateral control and students paired t-tests were performed.

Tables 1 through 5 show wound breaking strength data in Newtons, for each wound strip, at every harvested time point. The data are paired as cephalic, medial and caudate wounds, where agent C is the degradable DEAE Sephadex (test group) and is the saline (control group).

Figure 12:
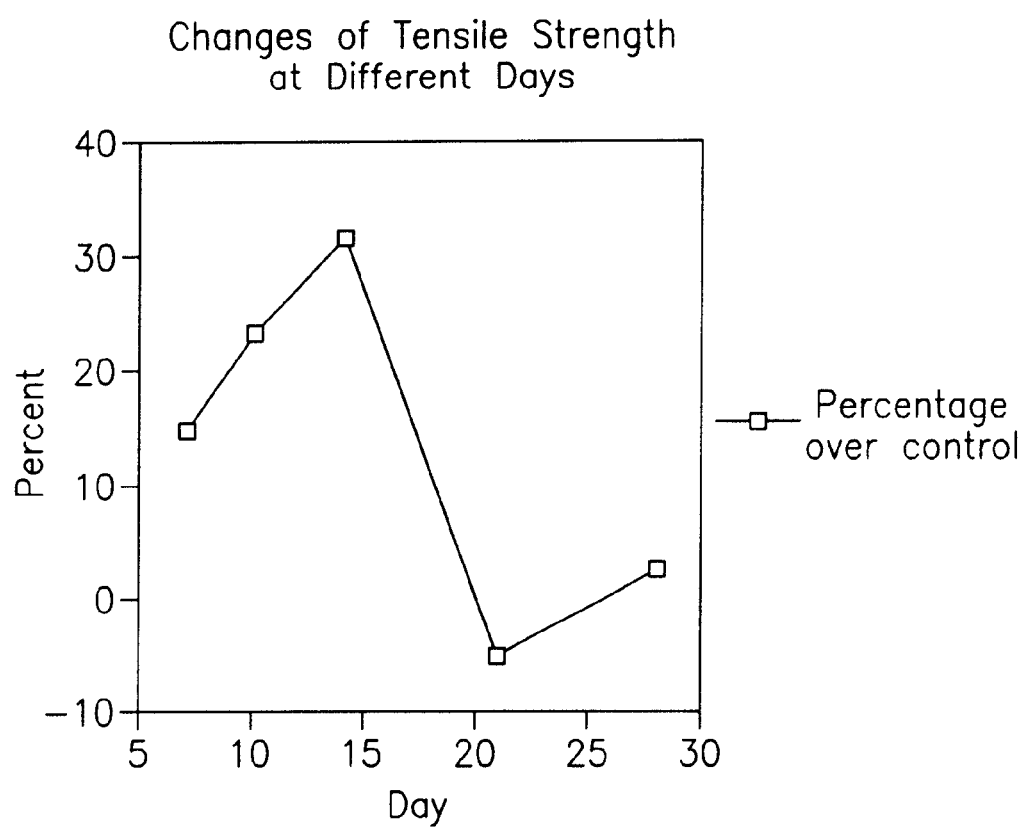
FIG. 12 is a graphical depiction of a percent change in the tensile strength of the DEAE Sephadex treated wounds compared to the control at various days in the study.

Paired student t-tests show a significant difference in wound breaking strength between treated and control wounds at days 7, 10 and 14. The magnitude of the effect is 14.62%, 23.25% and 31.27% increases in wound breaking strength for the degradable DEAE Sephadex treated wounds at days 7, 10 and 14 respectively. At days 21 and 28, there is no significant difference between treatment and control. These results are shown graphically in FIG. 12.

In this study a single application of degradable DEAE Sephadex at the time of wound closure was shown to increase wound strength at days 7, 10 and 14. However, wound breaking strength is equivalent for bead treated and control wounds beyond day 17. Histology shows that the material is degradable and biocompatible. Degradable DEAE Sephadex applied to wounds at the time of wound closure is a safe procedure which is well tolerated by rats.

Table 1 shows wound breaking strength data in Newtons for each DEAE Sephadex and control wound strip at day 7 post wounding. Table 2 shows wound breaking strength data in Newtons for each DEAE Sephadex and control wound strip at day 10 post wounding. Table 3 shows wound breaking strength data in Newtons for each DEAE Sephadex and control wound strip at day 14 post wounding. Table 4 shows wound breaking strength data in Newtons for each DEAE Sephadex and control wound strip at day 21 post wounding. Table 5 shows wound breaking strength data in Newtons for each DEAE Sephadex and control wound strip at day 28 post wounding.

It will be understood that various modifications may be made to the embodiments disclosed herein. For example, the compositions in accordance with this disclosure can be blended with other biocompatible, bioabsorbable or non-bioabsorbable materials. Any manner of surgical device can incorporate the charged polysaccharide. Therefore, the above description should not be construed as limiting, but merely as exemplifications of preferred embodiments. Those skilled in art will envision other modifications within the scope and spirit of the claims appended hereto.

TABLE 1

C/D (C-DEAE Sephadex; D-Control)) at Day 7

|  | C #1 | D #1 | C #2 | D #2 | C #3 | D #3 |
|---|---|---|---|---|---|---|
| Rat #1 | 3.202 | 3.215 | 3.869 | 3.035 | 3.649 | 3.669 |
| Rat #2 | 3.842 | 3.083 | 2.788 | 3.722 | 4.175 | 4.462 |
| Rat #3 | 5.286 | 4.788 | 5.035 | 4.207 | 2.842 | 4.282 |
| Rat #4 | 2.221 | 2.247 | 3.974 | 2.461 | 2.216 | 1.581 |
| Rat #5 | 4.392 | 2.521 | 3.694 | 2.687 | 4.886 | 2.053 |
| Rat #6 | 4.828 | 2.695 | 4.441 | 2.795 | 3.853 | 2.867 |
| Rat #7 | 2.895 | 3.664 | 3.387 | 2.812 | 3.717 | 3.276 |
| Rat #8 | 2.435 | 3.726 | 2.851 | 3.942 | 4.733 | 3.695 |
| Rat #9 | 4.869 | 3.038 | 2.935 | 4.069 | 2.795 | 3.756 |
| Rat #10 | 3.778 | 2.677 | 4.559 | 3.481 | 2.866 | 2.343 |
| Mean | 3.7748 | 3.1654 | 3.7533 | 3.3211 | 3.5732 | 3.1984 |
| Std Dev | 1.06912205 | 0.74084834 | 0.77317456 | 0.63906624 | 0.88303942 | 0.96178933 |
| Paired Student t Test |  | 0.03167586 |  |  |  |  |
| Percentage over control |  | 14.62% |  |  |  |  |

TABLE 2

C/D (C-DEAE Sephadex; D-Control) at Day 10

|  | C #1 | D #1 | C #2 | D #2 | C #3 | D #3 |
|---|---|---|---|---|---|---|
| Rat #1 | 6.597 | 5.723 | 6.016 | 5.056 | 6.791 | 5.836 |
| Rat #2 | 5.536 | 4.729 | 4.548 | 4.181 | 3.795 | 2.802 |
| Rat #3 | 6.003 | 5.596 | 5.942 | 3.195 | 5.796 | 5.105 |
| Rat #4 | 5.807 | 4.239 | 5.834 | 4.927 | 6.397 | 4.289 |
| Rat #5 | 5.298 | 4.017 | 6.195 | 2.957 | 6.221 | 3.218 |
| Rat #6 | 5.886 | 3.938 | 4.387 | 3.328 | 3.289 | 2.429 |
| Rat #7 | 3.186 | 3.386 | 2.847 | 4.931 | 3.729 | 5.338 |
| Rat #8 | 5.732 | 4.882 | 6.882 | 5.582 | 6.285 | 4.899 |
| Rat #9 | 4.197 | 2.185 | 3.578 | 3.229 | 4.539 | 3.513 |
| Rat #10 | 6.175 | 5.498 | 6.286 | 5.659 | 5.283 | 4.376 |
| Mean | 5.4417 | 4.4193 | 5.2515 | 4.3045 | 5.2125 | 4.1805 |

TABLE 2-continued

C/D (C-DEAE Sephadex; D-Control) at Day 10

|  | C #1 | D #1 | C #2 | D #2 | C #3 | D #3 |
|---|---|---|---|---|---|---|
| Std Dev | 1.0148688 | 1.10773363 | 1.32681593 | 1.05323251 | 1.28110224 | 1.14704444 |
| Paired Student t Test |  | 0.00106 |  |  |  |  |
| Percentage over control |  | 23.25% |  |  |  |  |

TABLE 3

C/D (C-DEAE Sephadex; D-Control) at Day 14

|  | C #1 | D #1 | C #2 | D #2 | C #3 | D #3 |
|---|---|---|---|---|---|---|
| Rat #1 | 10.475 | 7.496 | 8.932 | 7.121 | 9.486 | 7.837 |
| Rat #2 | 6.549 | 4.976 | 5.486 | 5.397 | 6.668 | 4.032 |
| Rat #3 | 9.244 | 6.905 | 10.369 | 7.834 | 7.486 | 5.334 |
| Rat #4 | 4.289 | 5.375 | 5.186 | 2.895 | 4.337 | 5.773 |
| Rat #5 | 7.275 | 3.265 | 6.758 | 4.605 | 5.338 | 3.693 |
| Rat #6 | 8.637 | 7.335 | 7.436 | 5.387 | 6.397 | 5.398 |
| Rat #7 | 5.487 | 3.887 | 7.595 | 4.312 | 7.421 | 4.504 |
| Rat #8 | 6.335 | 4.806 | 6.794 | 3.662 | 9.422 | 6.789 |
| Rat #9 | 7.597 | 4.486 | 8.29 | 6.442 | 7.719 | 5.351 |
| Rat #10 | 5.195 | 6.291 | 4.296 | 5.883 | 5.298 | 4.286 |
| Mean | 7.1083 | 5.4822 | 7.1142 | 5.3538 | 6.9572 | 5.2997 |
| Std Dev | 1.93356367 | 1.46609101 | 1.83048256 | 1.5382357 | 1.70563802 | 1.27987257 |
| Paired Student t Test |  | 0.00012666 |  |  |  |  |
| Percentage over control |  | 31.27% |  |  |  |  |

TABLE 4

C/D (C-DEAE Sephadex; D-Control) at Day 21

|  | C #1 | D #1 | C #2 | D #2 | C #3 | D #3 |
|---|---|---|---|---|---|---|
| Rat #1 | 18.458 | 16.773 | 15.118 | 17.741 | 14.147 | 18.713 |
| Rat #2 | 20.008 | 18.324 | 20.042 | 21.225 | 10.188 | 12.128 |
| Rat #3 | 17.093 | 13.055 | 12.939 | 13.639 | 17.394 | 17.834 |
| Rat #4 | 19.748 | 14.238 | 14.354 | 12.055 | 10.273 | 11.226 |
| Rat #5 | 12.335 | 19.375 | 10.365 | 17.639 | 9.194 | 15.327 |
| Rat #6 | 18.364 | 20.446 | 19.767 | 17.826 | 18.337 | 14.236 |
| Rat #7 | 11.765 | 12.687 | 15.829 | 16.202 | 14.374 | 16.832 |
| Rat #8 | 14.376 | 17.284 | 11.846 | 18.391 | 13.827 | 17.028 |
| Rat #9 | 17.449 | 11.769 | 15.695 | 20.162 | 17.238 | 18.827 |
| Rat #10 | 19.438 | 17.253 | 12.756 | 13.668 | 15.793 | 12.558 |
| Mean | 16.9034 | 16.1204 | 14.8711 | 16.8548 | 14.0765 | 15.4709 |
| Std Dev | 3.03130761 | 2.99786495 | 3.16746665 | 2.95711894 | 3.26055037 | 2.80596276 |
| Paired Student t Test |  | 0.2816429 |  |  |  |  |
| Percentage over control |  | −5.35% |  |  |  |  |

TABLE 5

C/D (C-DEAE Sephadex; D-Control) at Day 28

|  | C #1 | D #1 | C #2 | D #2 | C #3 | D #3 |
|---|---|---|---|---|---|---|
| Rat #1 | 29.045 | 27.395 | 24.193 | 26.193 | 27.394 | 25.834 |
| Rat #2 | 25.495 | 22.194 | 28.394 | 22.394 | 26.295 | 24.164 |
| Rat #3 | 34.291 | 31.201 | 32.119 | 30.183 | 31.038 | 28.371 |
| Rat #4 | 28.464 | 29.934 | 27.925 | 32.849 | 25.355 | 30.284 |
| Rat #5 | 24.047 | 25.284 | 22.283 | 23.956 | 28.374 | 26.331 |
| Rat #6 | 29.338 | 23.183 | 27.334 | 28.574 | 22.219 | 27.384 |
| Rat #7 | 30.234 | 31.394 | 28.586 | 26.445 | 33.921 | 25.236 |
| Rat #8 | 32.747 | 29.384 | 33.194 | 34.295 | 32.185 | 30.182 |
| Rat #9 | 25.394 | 26.338 | 24.283 | 32.471 | 26.483 | 29.745 |
| Rat #10 | 32.918 | 25.184 | 30.184 | 29.221 | 27.112 | 25.383 |
| Mean | 29.1973 | 27.1491 | 27.8495 | 28.6581 | 28.0376 | 27.2914 |
| Std Dev | 3.47599597 | 3.2579654 | 3.50283045 | 3.92780633 | 3.47543328 | 2.24101069 |
| Paired Student t Test |  | 0.44053042 |  |  |  |  |
| Percentage over control |  | 2.38% |  |  |  |  |

What is claimed is:

1. A method of reducing scar formation at a wound site comprising:
   providing a TGF-β reducing amount of a cross-linked polysaccharide having a positive charge; and
   contacting the wound site with an effective TGF-β reducing amount of a cross-linked polysaccharide having a positive charge to a locus having TGF-β activity and allowing the wound site to heal thereby reducing scar formation at the healing site.

2. A method of reducing scar formation at a wound site according to claim 1 wherein the polysaccharide is a cross-linked dextran.

3. A method of reducing scar formation at a wound site according to claim 2 wherein the cross-linked dextran is bioabsorbable.

4. A method of reducing scar formation at a wound site according to claim 3 wherein the cross-linked dextran is oxidized.

5. A method of reducing scar formation at a wound site according to claim 1 wherein the polysaccharide is contained within a pharmaceutically acceptable vehicle.

6. A method of reducing scar formation at a wound site according to claim 5 wherein the composition is a powder.

7. A method of reducing scar formation at a wound site according to claim 5 wherein the composition is a gel.

8. A method of reducing scar formation at a wound site according to claim 5 wherein the composition is a non-polar fluid.

9. A method of reducing scar formation at a wound site according to claim 1 wherein the positive charge is provided by diethylaminoethyl moieties.

10. A biocompatible surgical device comprising a structure adapted to contact living tissue at a locus having TGF-β activity, the structure having a TGF-β reducing amount of a cross-linked polysaccharide having a positive charge.

11. A method of reducing the activity of TGF-β comprising applying an effective TGF-β activity reducing amount of a cross-linked polysaccharide having a positive charge to a locus having TGF-β activity.

12. A method of reducing the activity of TGF-β according to claim 11 wherein the polysaccharide is a cross-linked dextran.

13. A method of reducing the activity of TGF-β according to claim 12 wherein the cross-linked dextran is bioabsorbable.

14. A method of reducing the activity of TGF-β according to claim 13 wherein the cross-linked dextran is oxidized.

15. A method of reducing the activity of TGF-β according to claim 11 wherein the polysaccharide is contained in a composition including a pharmaceutically acceptable vehicle.

16. A method of reducing the activity of TGF-β according to claim 11 wherein the positive charge is provided by diethylaminoethyl moieties.

17. A method of increasing wound strength at a wound site for the first about 17 days of healing comprising:
   providing a TGF-β reducing amount of a cross-linked polysaccharide having a positive charge; and
   contacting the wound site with an effective TGF-β reducing amount of a cross-linked polysaccharide having a positive charge to a locus having TGF-β activity and allowing the wound site to heal thereby strengthening the wound at the healing site.

* * * * *